United States Patent [19]

Fujiwara et al.

[11] Patent Number: 5,202,479

[45] Date of Patent: Apr. 13, 1993

[54] PROCESS FOR PREPARING GLYCINE

[75] Inventors: Kenji Fujiwara; Nobutaka Ueda; Yuji Matsuu; Hiroshi Kato; Atsuhiko Hiai, all of Osaka, Japan

[73] Assignee: Mitsui Toatsu Chemicals, Inc., Tokyo, Japan

[21] Appl. No.: 649,021

[22] Filed: Feb. 1, 1991

[30] Foreign Application Priority Data

Feb. 6, 1990 [JP] Japan .................................. 2-25266
Feb. 6, 1990 [JP] Japan .................................. 2-25267
Oct. 15, 1990 [JP] Japan .................................. 2-273282

[51] Int. Cl.$^5$ ................. C07C 101/06; C07C 229/08; C07C 227/12
[52] U.S. Cl. ..................................... 562/575; 562/550
[58] Field of Search ............................... 562/575, 550

[56] References Cited

U.S. PATENT DOCUMENTS 3,536,726 10/1970 Fink et al. ............................. 546/335

FOREIGN PATENT DOCUMENTS 2195625 3/1974 France .

OTHER PUBLICATIONS

Patent Abstracts of Japan, unexamined applications, C field, vol. 14, No. 571, Dec. 19, 1990, pp. 141 C 790.
Patent Abstrats of Japan, unexamined applications, C section, vol. 2, No. 76, Jun. 16, 1978, p. 890 C 78.
Chemical Abstracts, 82, 171440r (1975); and JPA 49-127915, Dec. 7, 1974.
Chemical Abstracts, 89, 24804d (1978); and JPA 53-28116, Mar. 16, 1978.

*Primary Examiner*—Arthur C. Prescott
*Attorney, Agent, or Firm*—Burns, Doane, Swecker & Mathis

[57] ABSTRACT

A process for preparing glycine which comprises the steps of reacting glycolonitrile, carbon dioxide gas, ammonia and water to obtain a reaction solution containing glycine, concentrating this reaction solution in two steps, recycling a gaseous phase portion formed in a primary concentration step to a reaction zone, and recycling to the reaction zone, a mother liquor left after glycine crystals have been separated from a concentrate obtained in a secondary concentration step.

13 Claims, No Drawings

PROCESS FOR PREPARING GLYCINE

BACKGROUND OF THE INVENTION (a) Field of the Invention

The present invention relates to a process for directly preparing glycine from glycolonitrile via hydantoin, and more specifically it relates to a process for obtaining glycine by the reaction of glycolonitrile, ammonia and carbon dioxide.

(b) Description of the Related Art

Glycine is a useful compound which is widely used as a raw material for food additives for processed foodstuffs, agricultural chemicals and medicines.

Heretofore, as methods for manufacturing glycine, there have been mainly known an amination method using monochloroacetic acid, a Strecker method, a hydantoin method and the like.

The Strecker method comprises reacting ammonia with glycolonitrile which can be synthesized substantially quantitatively from hydrocyanic acid and formalin, carrying out hydrolysis with an alkali such as NaOH to form a metal salt of glycine, and then removing the metal with an acid such as sulfuric acid to prepare free glycine. In this method, the separation of a neutral salt such as sodium sulfate is necessary after the hydrolysis, and the treatment of this salt impairs economy substantially.

On the other hand, the above-mentioned hydantoin method comprises reacting glycolonitrile, which can be synthesized from hydrocyanic acid and formaldehyde, with ammonia and carbon dioxide gas in the presence of water to form hydantoin, and then hydrolyzing the same to prepare glycine When an alkali such as NaOH is used in the hydrolysis, the separation and treatment of sodium sulfate are necessary, as in the Strecker method. In this hydantoin method, there is a process for directly obtaining free glycine without using an alkali such as sodium hydroxide (hereinafter referred to as "the hydantoin-via direct method"), and this hydantoin-via direct method is an economical process for the preparation of glycine without a by-product such as sodium sulfate and without environmental pollution.

As some examples of such a hydantoin-via direct method, there have been known a method in which hydrogen cyanide, aldehyde, ammonia and carbon dioxide are heated at 100° C. or more in an aqueous medium (U.S. Pat. No. 3,536,726), a method in which hydrogen cyanide, formaldehyde and ammonium carbonate are heated in an aqueous medium (Japanese Patent Laid-open No. 49-127915), a method in which glycolonitrile, ammonia and carbon dioxide are heated to remove ammonia and carbon dioxide, followed by a treatment with an alkylamine or an alkylammonium hydroxide, and a method in which glycolonitrile, ammonia and carbon dioxide are heated to remove ammonia and carbon dioxide, followed by a treatment with a mineral acid to effect hydrolysis (Japanese Patent Laid-open No. 53-28116). In U.S. Pat. No. 3,538,726, it is also disclosed that most of the glycine is separated from a reaction solution, and the remaining solution (hereinafter referred to simply as "mother liquor") is returned to a reaction zone.

However, these methods mainly intend to improve the yield of each reaction, and they do not provide any techniques for industrially manufacturing glycine inclusive of the separation manner of ammonia and carbon dioxide, the concentration manner of the reaction solution and the recycling manner of the ammonia, carbon dioxide and mother liquor.

According to the investigation by the present inventors, the following has been found: In the step of concentrating the reaction solution obtained by the hydantoin-via direct method, to isolate glycine from it, a normal heating treatment for concentration of it makes the isolation of glycine impossible. Additionally, at this time, by-products such as 2,5-diketopiperazine having extremely low solubility in water increase perceptibly, so that it is practically impossible to isolate glycine from these kinds of by-products.

Furthermore, the present inventors have found that the employment of glycolonitrile containing water (or an aqueous glycolonitrile solution) prevents the decomposition of glycolonitrile and a side reaction by which a colored material is formed. The reaction of the present invention stoichiometrically produces 1 mole of glycine from 1 mole of glycollonitrile and 1 mole of water, and therefore it consumes water, but the amount of water which is consumed by the reaction is small. Therefore, when the water-containing glycolonitrile (or the aqueous glycolonitrile solution) is used which is a preferable feed morphology in that the decomposition of the glycolonitrile is prevented, water corresponding to the contained water therein is excessive, so that it is accumulated in the system. That is, it is required to purge water corresponding to the excess water from the system. However, the method for purging water containing the carbon dioxide and ammonia or the mother liquor from the system is not economical, and such a purge of the carbon dioxide and ammonia or organic materials in the mother liquor from the system is also undesirable from the viewpoint of environmental pollution. Therefore, the present inventors have found that a process for preparing high-purity glycine in a high yield substantially without discarding ammonia and the carbon dioxide or the organic materials is essential to industrially manufacture glycine.

The present inventors have intensively conducted research on a process for preparing glycine in a high yield by concentrating a reaction solution effectively in accordance with the hydantoin-via direct method, and as a result, the present invention was made.

SUMMARY OF THE INVENTION

According to one aspect of the present invention, there is provided a process for preparing glycine by reacting glycolonitrile, carbon dioxide, ammonia and water which comprises:

reacting glycolonitrile, carbon dioxide, ammonia and water at a high temperature to obtain a reaction solution containing glycine; and concentrating the thus obtained reaction solution to remove water under conditions of a temperature and a time represented by the formula $$\ln(\tau) < (16800/T) - 37.8$$

[wherein $\tau$ and T mean the time (minute) and the temperature (°K.)], thereby separating glycine.

According to another aspect of the present invention, there is provided a process for preparing glycine by reacting glycolonitrile, carbon dioxide, ammonia and water which comprises the steps of:

(a) feeding glycolonitrile, carbon dioxide, ammonia and water to a reaction zone and then reacting them at a high temperature to obtain a reaction solution containing glycine;

(b) concentrating the reaction solution thereby obtaining a gaseous phase portion comprising carbon dioxide, ammonia and water, and a liquid phase portion (a primary concentrate);

(c) recycling the gaseous phase portion to the reaction zone;

(d) further concentrating the primary concentrate thereby obtaining a gaseous phase portion mainly comprising water and a liquid phase portion (a secondary concentrate);

(e) purging at least a part of the gaseous phase portion from the system;

(f) crystallizing glycine from the secondary concentrate to obtain a slurry containing glycine crystals;

(g) separating the slurry into the glycine crystals and a mother liquor; and (h) recycling at least a part of the mother liquor to the reaction zone.

DETAILED DESCRIPTION OF THE INVENTION

Glycolonitrile used in the present invention can be directly used without an additional treatment. The present inventors have found that glycolonitrile containing a relatively large amount of water is preferable, because the self-decomposition of glycolonitrile can be controlled so as to heighten the yield of glycine in a synthetic reaction and to inhibit the formation of by-products such as colored materials. However, it is not preferable that the content of water is too large, since a large amount of energy is required to remove water after the reaction. Accordingly, when an aqueous glycolonitrile solution is used, its concentration is preferably from about 30 to about 70% by weight. This kind of aqueous glycolonitrile solution can be produced by the most usual and economical manufacturing method in which hydrocyanic acid and water-containing formalin are used as raw materials, but it is also possible to use a formalin source prepared by dissolving paraformaldehyde in water. The formation reaction of glycolonitrile is extremely fast, and therefore, for example, glycolonitrile can be easily produced only by blowing a hydrocyanic acid gas into an aqueous formalin solution or mixing an aqueous hydrocyanic acid solution with the aqueous formalin solution In this case, the reaction temperature is usually in the range of from about 0° to about 80° C. and time is usually in the range of from about 2 minutes to about 5 hours. Furthermore, glycolonitrile, when used, may contain sulfuric acid or phosphoric acid which can be used as a stabilizer.

Ammonia and carbon dioxide used in the process of the present invention may be directly used without any modification, but instead, known compounds such as ammonium carbonate or ammonium bicarbonate may be used which can produce ammonia and carbon dioxide under reaction conditions. In addition, when these compounds are used in the form of a mixture, preferable results can be similarly obtained.

In the process of the present invention, the amount of ammonia to be used is in the range of from 1 to 12 moles, preferably from 4 to 9 moles based on one mole of glycolonitrile. When the amount of ammonia is less than 1 mole, the reaction is slow, and when it is more than 12 moles, the amount of by-products increases and reaction pressure also increases unpreferably, though the reaction rate is accelerated.

The amount of the carbon dioxide to be used is from ⅛ to 3 moles based on one mole of ammonia. It is preferred that the amount of the carbon dioxide is in this range, since the reaction rate is fast and the reaction pressure is low.

In the method of the present invention, the amount of water to be used is in the range of from 5 to 15 moles based on one mole of ammonia. When the amount of water is less than 5 moles, the selectivity of glycine produced is very low and, glycine having a very low purity is crystallized if the crystallization ratio (the ratio of isolated glycine to glycine in the reaction solution) of glycine is not kept extremely small. On the other hand, when water is used in an amount in excess of 15 moles, the selectivity of glycine increases, but the concentration of glycine in the reaction solution decreases, so that the cost of the concentration for the crystallization increases and an uneconomically large reactor is required.

In the present invention, when the reaction temperature is low, the selectivity of glycine is high but the reaction rate is slow Therefore, it is preferred that the reaction temperature is high. That is, the reaction temperature is usually from 100° to 200° C., preferably from 140° to 180° C., more preferably from 150° to 170° C. In this connection, the reaction time is usually from about 30 minutes to about 20 hours, preferably from about 1 hour to about 10 hours.

In the present invention, no particular restriction is put on the reaction pressure, and the reaction can be carried out under a pressure higher than the pressure generated during the reaction and it can also be carried out while ammonia, carbon dioxide or a solvent vapor generated during the reaction is suitably drawn off.

The present inventors have found that glycolonitrile which is the raw material is not usually substantially present at all in the reaction solution containing glycine after the reaction which can be obtained by the process of the present invention, but in this reaction solution, there are contained, in addition to glycine, by-products such as hydantoic acid, glycyl glycine, hydantoic amide, triglycine, hydantoin and 2,5-diketopiperazine. Glycine can be separated from this reaction solution by a means such as crystallization which will be described in detail later. Moreover, the present inventors have found that the yield of glycine can be remarkably improved by recycling a mother liquor after the separation of glycine and the by-products contained therein to the reaction zone (hereinafter referred to as "reactor") which comprises water, glycolonitrile, the carbon dioxide gas and ammonia. This is considered to be due to the novel knowledge discovered by the present inventors that the equilibrium between these by-products and glycine shifts toward the glycine side as much as the amount of glycine separated and removed by the crystallization or the like, when the mother liquor is recycled to the reactor. In consequence, when the mother liquor is recycled to the reactor (hereinafter referred to as "mother liquor recycle process"), the isolated yield of glycine, which is isolated in the form of crystals, based on glycolonitrile is remarkably improved, and it is high, 75% or more. In case that the mother liquor is not recycled, the yield of one-pass glycine is high but the yield of glycine isolated as the crystals is actually at most about 60%.

That is, it can be considered that, to say the least of it, the above-mentioned by-products can be converted into glycine under reaction conditions defined by the present invention.

The reaction solution obtained under the above-mentioned conditions preferably by the mother liquor recycle process is flashed and/or heated at a temperature of from about 50° to about 200° C. under a pressure of from about 10 mm Hg to about 30 Kg/cm² so as to evaporate water and thereby concentrate the reaction solution. At this time, usually, ammonia and carbon dioxide are also vaporized and separated from the reaction solution. That is, the reaction solution is separated into a gaseous phase portion comprising carbon dioxide, ammonia and water and a liquid phase portion. Alternatively, air or an inert gas such as nitrogen may be bubbled into the reaction solution at a temperature of from 50° to 200° C. under a pressure of from 10 mm Hg to 30 kg/cm² in order to strip the carbon dioxide and ammonia from the reaction solution, whereby they can be separated therefrom. However, a separation manner other than the above-mentioned procedure can also be used without any restriction. The concentration of the reaction solution is carried out for a period of from about 10 seconds to about 20 hours, preferably about 1 minute to about 10 hours.

The present inventors have also found the following: When the separation of the carbon dioxide and ammonia from the concentrate is insufficient, they are precipitated as ammonium carbonate and adhere to the glycine crystals in the step for crystallizing glycine from the concentrate so as to separate glycine. As a result, the amount of the colored mother liquor which adheres to the glycine crystals is larger than in the case where sufficient separation of carbon dioxide and ammonia is made, and thus a large amount of rinse water is necessary. Therefore, it is preferred that the reaction solution is concentrated so that the concentration of the remaining carbon dioxide and ammonia may be 10% by weight or less in terms of ammonium carbonate.

When the concentration temperature is less than 50° C., it is too low for separated carbon dioxide and ammonia to be condensed. In order to effectively utilize the heat source of the gaseous phase portion in the concentration, the concentration temperature is 80° C. or more, preferably 120° C. or more. However, the present inventors have found that when the concentration temperature is in excess of 200° C., the coloration of the concentrate is facilitated noticeably. Therefore, the concentration temperature is preferably from 50° to 200° C., more preferably from 80° to 180° C.

According to the investigation by the present inventors, it have been found that the formation rate of by-products such as 2,5-diketopiperazine which are formed in the concentration step is scarcely affected by the concentration of glycine but is largely influenced by concentration temperature and residence time in the concentration step. As a result of the detailed study regarding the concentration temperature and the residence time, the present inventors have also found that the formation of such by-products can be prevented by controlling the concentration time in view of the concentration temperature. That is, the relation between the temperature and the time in the concentration step preferably meets the formula (I)

$$\ln(\tau) < (16800/T) - 37.8 \tag{I}$$

[wherein $\tau$ and T mean the time (minute) and the temperature (°K.)].

In this connection, the lower limit of the time $\tau$ preferably meets $-1.8 < \ln(\tau)$ from the viewpoint of a concentration device. The thus concentrated reaction solution is cooled, and glycine is then crystallized and separated therefrom. At this time, the remaining mother liquor is recycled to the reactor, whereby the yield of isolated glycine can be remarkably increased. When the above-mentioned relation is not met, not only the yield of glycine becomes low but also by-products such as 2,5-diketopiperazine having an extremely low solubility in water increase noticeably, and these by-products are crystallized together with glycine, with the result that the separation of glycine from the by-products is practically impossible. However, judging from the fact that even when an aqueous solution of pure glycine is only heated and concentrated, the amount of the by-products of 2,5-diketopiperazine and the like is much smaller than in the case when the reaction solution obtained by the recycle of the mother liquor is heated, it can be presumed that the increase of the by-products in the concentration step is due to, in the heating and concentration steps, the change of the by-products other than 2,5-diketopiperazine accumulated in the reaction solution during the recycle of the mother liquor. The present inventors have found that most of these by-products accumulated in the reaction solution are useful compounds which can be converted into glycine under the reaction conditions where the carbon dioxide and ammonia are present, which will be described hereinafter. However, the by-products which are difficult to separate from glycine increase noticeably in the concentration step, depending upon conditions. The present inventors have also found that a crucial difference between such reaction conditions and the concentration conditions resides in the amounts of the existing carbon dioxide and ammonia. This has been confirmed by the fact that the by-products formed in the concentration step return to compositions before this step, and that the yield of glycine also returns to before this step when the reaction is carried out under the reaction conditions.

In the present invention, the carbon dioxide and ammonia separated from the reaction solution can be economically reused. Preferably, the carbon dioxide, ammonia and water is cooled and condensed at a temperature of the concentration temperature or less, and the resulting condensate is recovered in the form of an aqueous solution and then recycled to the reactor. In the case where ammonia and the carbon dioxide are stripped by the use of an inert gas such as air or nitrogen, the inert gas can conveniently be separated from the aqueous solution containing the condensed carbon dioxide and ammonia.

In the process of the present invention, the carbon dioxide and ammonia which have been separated by concentrating the reaction solution are recycled to the reactor, and the mother liquor which is the concentrate from which glycine has been separated is also preferably recycled to the reactor. However, glycolonitrile is preferably fed in the form of an aqueous glycolonitrile solution, but in the present reaction, water is consumed as much as 1 mole to 1 mole of glycolonitrile. Thus, water associated with glycolonitrile is excessive.

In the process of the present invention, the reaction solution is concentrated in the two steps, whereby the excess water can be purged effectively from the system. That is, in the first condensation step, the vaporization of water is controlled to the utmost, but at least 80% by weight of ammonia, 80% by weight or more of the carbon dioxide and 50 to 90% by weight of water are vaporized in order to obtain a gaseous phase portion comprising carbon dioxide gas, ammonia and water as well as a liquid phase portion (a primary condensate) (this operation will be referred to as "primary condensation step"). Next, in the second concentration step, the reaction solution is further concentrated, and water containing small amounts of ammonia and carbon dioxide gas is vaporized in order to obtain a gaseous phase portion mainly comprising water and a liquid phase portion (a secondary condensate) (this operation will be referred to as "secondary condensation step"). The gaseous phase portion (ammonia, carbon dioxide and water) in the above-mentioned primary condensation step is recycled to the reactor, and the gaseous phase portion (most of which comprises water) in the secondary condensation step is purged from the system as much as at least an amount corresponding to that of the above-mentioned excess water. In the primary and secondary condensation steps, the condensation temperature and the condensation time are preferably adjusted so as to meet the above-mentioned formula (I).

In the primary condensation step in the process of the present invention, the obtained reaction solution is first distilled at about 50° to about 200° C. under about 10 mm Hg to about 30 Kg/cm$^2$ by the use of a distillation column or a stripper having a suitable theoretical plate number, for example, 2 to 30 plates in order to separate, from the reaction solution, 80% by weight or more, preferably 90% by weight or more, more preferably 95% by weight or more, most preferably 98% by weight or more to substantially 100% by weight of ammonia and the carbon dioxide. Simultaneously, 10 to 90% by weight of water is also vaporized from the reaction solution to concentrate the same. In this case, it is acceptable that water can be retained in an amount corresponding to that of the above-mentioned excess water or more in the primary concentrate, and it and unpreferably requires expensive distillation column to control the amount of vaporized water so as to be less than 10% by weight. Therefore, it is usually preferred that 10 to 90% by weight, preferably 20 to 80% of water is vaporized from the reaction solution so as to regulate the concentration of glycine to from 5 to 35% by weight, preferably from 8 to 33% by weight. The amounts of ammonia, carbon dioxide gas and water which should be vaporized from the reaction solution can be optionally controlled by adjusting the theoretical plate number of the distillation column or the stripper. The separated carbon dioxide and ammonia are recycled to the reactor for reaction.

In the present invention, the secondary concentration step in which the primary concentrate is further concentrated is typically identical with the primary concentration step, but it is not necessary to adjust the vaporization ratio of ammonia, carbon dioxide and water. Accordingly, a device for the secondary concentration step may be simpler than a device used in the primary concentration step. The secondary concentration step may be constituted so that only flashing and/or heating may be carried out at about 50° to about 200° C. under about 10 mm Hg to about 30 Kg/cm$^2$. Usually, in the secondary concentration step, 10 to 90% by weight, preferably 15 to 80% of water is vaporized from the primary concentrate so as to increase the concentration of glycine up to 10 to 40% by weight, preferably 15 to 35% by weight At this time, water in the gaseous phase portion is purged from the system as much as an amount corresponding to that of the above-mentioned excess water. The remaining water can be utilized as rinse water in a solid-liquid separation step after the crystallization step or as water for dissolving glycine therein. Incidentally, in the primary concentration step, it is also possible to employ the stripping with an inert gas such as nitrogen.

Next, the secondary concentrate can be cooled to, for example, about 0° to about 80° C., thereby crystallizing glycine. In order to crystallize glycine from this concentrate, a known technique can be industrially preferably used which is, for example, a cooling crystallization method, a vaporization crystallization method or a vacuum crystallization method. Furthermore, when a method in which the concentrating operation is performed simultaneously with the crystallization, for example, the vaporization crystallization method or the vacuum crystallization method is used, water in the concentration step can be purged from the system, and thus the secondary concentration and the crystallization of glycine can be simultaneously achieved.

The slurry obtained by this crystallization is then separated into the glycine crystals and the mother liquor by the use of a prevalent separator. In this case, a crystallization ratio is preferably 40% by weight or more. When this crystallization ratio is less than 40% by weight, the amount of the mother liquor which is recycled increases, with the result that the unduly large reactor is required and a concentration cost for the crystallization also increases. However, when the crystallization ratio is 40% by weight or more, glycine having a purity of 95% by weight or more can be obtained.

Furthermore, it is also possible to add a crude solvent such as methanol to the concentrate prior to the crystallization, but in this case, methanol is distilled and separated from the mother liquor and the thus recovered methanol is reused. At least a part of the mother liquor left after the separation of the crystals is recycled to the reactor. The amount of the mother liquor to be recycled is 40% by weight or more, preferably 60% by weight or more, more preferably 90% by weight or more and 100% by weight or less.

In the present invention, for the purpose of decreasing the concentration cost, the concentration can be carried out in succession in a usual multiple effect evaporator, and when there is used a method in which in the secondary concentration step, the gaseous phase portion is purged from the system according to the present invention, more preferable results can be obtained.

Preferably, the thus obtained glycine crystals are further dissolved in water, and the resulting aqueous glycine solution is then treated for decoloration. Typically, the decoloration can be achieved by using active carbon, an ion exchange resin, an active clay or the like, and crystallization is then carried out in like manner, thereby obtaining colorless and high-quality glycine in which the hue is improved. The above-mentioned decoloration is accomplished by the use of active carbon, an ion exchange resin or the like.

The active carbon used in the present invention may be what is made of a mineral such as a coal or a pitch, or a plant such as coconut shells. The morphology of the usable active carbon may be powder or grains. Exemplary trade names of the commercially available active carbons include Shirasagi C (Takeda Chemical Industries, Ltd.), Tsurumicol HC-30 (Tsurumi Co., Ltd.), CPG and CAL (Toyo Karugon Co., Ltd.) and A-BAG (Kureha Chemical Industry Co., Ltd.).

Examples of the ion exchange resin used in the present invention include strongly basic anion exchange resins, moderately basic anion exchange resins, weakly basic anion exchange resins, strongly acidic cation exchange resins, weakly acidic cation exchange resins and ion exchange resins having no exchange group In this connection, the ion type of the ion exchange resin may be a salt type, but an OH type and an H type are preferable.

The usable ion exchange resins are commercially available under the following trade names: Rebatit M500, MP500, MP500A, Amberlite IRA01, IRA402, IRA402BL, IRA400T, IRA430, IRA68, IRA93, IR116, IRC84, Diaion SA10A, SA11A, SA20A, SA21A, PA306, PA308 and PA312.

In the process of the present invention, the treatment of the aqueous crude glycine solution with the active carbon or the ion exchange resin can be carried out in accordance with a usual procedure.

For example, in case that the active carbon or the ion exchange resin is used in a flow system, a suitable cylindrical container is packed with the active carbon or the ion exchange resin and the liquid to be decolored is continuously caused to run through the container as know in the art. Preferably, the packing is effected so that the active carbon or the ion exchange resin may be effectively used. The ratio of packing length/diameter is in the range of from 2 to 20. Furthermore, a preferable treatment rate is in the range of from 0.1 to 20 $(hr^{-1})$ in terms of SV (space velocity), but this range is not restrictive.

In the decoloration step of the present invention, the concentration of the aqueous glycine solution can be optionally selected, but it is preferably from about 5 to about 30% by weight from the viewpoint of handling. When the concentration of the aqueous glycine solution is less than this range, the concentration cost of the aqueous glycine solution subsequent to the decoloration increases. Conversely, when it is in excess of the above-mentioned range, it is required to maintain a certain temperature for the purpose of preventing the crystallization during the treatment.

Moreover, no particular restriction is put on the decoloration temperature. According to some experiments by the present inventors, any difference of the decoloration performance has not been perceived in the range of from about 20° to about 80° C. In consequence, in the process of the present invention, the decoloration can be achieved at any temperature in the range of from about 20° to about 80° C.

In the process of the present invention, the active carbon and the ion exchange resin can be used together so as to further improve the effect of the decoloration The thus decolored aqueous glycine solution can be treated by a known method such as the above-mentioned crystallization in order to obtain high-purity glycine.

The process of the present invention can be achieved by a batch system, a semi-flow system or a flow system.

Now, the present invention will be described in detail in reference to examples. It is to be noted that the scope of the present invention should not limited to these examples.

EXAMPLE 1

A mixture of 230 g (2.01 moles) of a 50% by weight aqueous glycollonitrile solution, 206 g (12.1 mols) of ammonia and 267 g (6.1 moles) of a carbon dioxide per hour was fed to a pipe type reactor having an internal volume of 10 liters. Reaction was carried out at a reaction temperature of 150° C. under a reaction pressure of 50 kg/cm². At this time, the composition of the raw materials was $H_2O/NH_3/CO_2$/glycolonitrile=45/6/3/1 in terms of molar ratio, and an average residence time was 5 hours. When a steady state was reached, the reaction solution was concentrated in a concentrator so as to remove water, ammonia and a carbon dioxide, followed by crystallization, whereby 0.89 mole (purity 98.2%) of glycine per hour was separated. The remaining mother liquor was analyzed, and as a result, 0.97 mole of hydantoic acid, glycylglycine, hydantoic amide, 2,5-diketopiperazine, hydantoin, triglycine and glycine in all in terms of glycolonitrile were detected. The mother liquor for an initial feed was prepared in this way.

Next, this mother liquor, a 50% by weight aqueous glycolonitrile solution and an aqueous ammonium carbonate solution were fed to a reactor so that the composition of these components might be identical with the feed composition in terms of glycolonitrile. That is, an aqueous solution containing this mother liquor, 118 g (1.04 moles) of the 50% by weight aqueous glycolonitrile solution and 6.1 moles of ammonium carbonate was fed to the reactor. The resulting reaction solution was continuously concentrated by the use of the concentrator at a concentration temperature of 130° C. for a concentration time of 10 minutes which met the requirements prescribed by the formula (I) (the concentration was achieved by one step). In consequence, most of water, ammonia and the carbon dioxide were removed from the reaction solution, and crystallization was then made at 5° C., so that 68 g (purity 98.6%) of glycine per hour was separated (in this case, water, ammonia and the carbon dioxide were not recycled to the reactor). This amount of the crystallized glycine corresponded to 58% by weight of glycine in the reaction solution, and hence the yield of glycine isolated was 86%.

Comparative Example 1

The same procedure as in Example 1 was effected except that concentration was carried out at a concentration temperature of 130° C. for a concentration time of 90 minutes which did not meet the requirements prescribed by the formula (I), so that 65 g of glycine per hour was obtained, but its purity was very low, 88 9%. This glycine was further recrystallized, but the purity was scarcely improved.

EXAMPLE 2

The same procedure as in Example 1 was effected except that concentration was carried out at a concentration temperature of 120° C. for a concentration time of 60 minutes which met the requirements prescribed by the formula (I), so that 67 g of glycine per hour was obtained, and its purity was 98.3%.

Comparative Example 2

The same procedure as in Example 2 was effected except that concentration was carried out at a concentration temperature of 120° C. for a concentration time of 180 minutes which did not meet the requirements prescribed by the formula (I), so that 68 g of glycine per hour was obtained, but its purity was very low, 89.3%. This glycine was further recrystallized, but the purity was scarcely improved.

EXAMPLE 3

The same procedure as in Example 1 was effected except that concentration was carried out at a concentration temperature of 140° C. for a concentration time of 5 minutes which met the requirements prescribed by the formula (I), so that 62 g of glycine per hour was obtained, and its purity was 98.5%.

Comparative Example 3

The same procedure as in Example 3 was effected except that concentration was carried out at a concentration temperature of 140° C. for a concentration time of 30 minutes which did not meet the requirements prescribed by the formula (I), so that 62 g of glycine per hour was obtained, but its purity was very low, 86.1%. This glycine was further recrystallized, but the purity was scarcely improved.

Comparative Example 4

The same procedure as in Example 1 was effected except that concentration was carried out at a concentration temperature of 190° C. for a concentration time of 1 minute which did not meet the requirements prescribed by the formula (I), so that 56 g of glycine per hour was obtained, but its purity was very low, 85.2%. This glycine was further recrystallized, but the purity was scarcely improved, and additionally coloring was noticeable.

EXAMPLE 4

A manufacturing apparatus was used which comprises a tube type reactor having an internal volume of 10 liters, and on its downstream side, a condenser having an internal volume of 3 liters and a carbon dioxide/ammonia absorbing column having a diameter of 15 cm and a height of 1.5 m. An aqueous solution containing 5.18% by weight of glycolonitrile, 9.3% by weight of ammonia and 12.03% by weight of a carbon dioxide was fed to the reactor in a feed ratio of 2220 g of this aqueous solution per hour, and reaction was then carried out at a reaction temperature of 150° C. under a reaction pressure of 32 kg/cm$^2$. Glycolonitrile was used in the form of a 50% by weight aqueous solution and the feed of glycolonitrile was 2.01 moles per hour. The composition of the raw materials was $H_2O/NH_3/CO_2$/glycolonitrile=45/6/3/1 in terms of molar ratio, and an average residence time was 5 hours. When a steady state was reached, the reaction solution was concentrated at 100° C. for a residence time of 2 hours (the primary concentration step), adjusting steam for heating so that the concentration of glycine might be 27% by weight. The resulting gaseous phase portion was cooled and condensed, thereby recovering 1780 g of an aqueous solution for an initial feed per hour which contained the carbon dioxide and ammonia. Each recovery of the carbon dioxide and ammonia was 98% by weight or more.

On the other hand, the concentrate (the primary condensate) obtained in a ratio of 440 g/hour contained 117.5 g of glycine. This concentrate was further concentrated at 120° C. for a residence time of 15 minutes (the secondary concentration step) so that the concentration of glycine might be 30% by weight, and the resulting secondary concentrate was then cooled at 5° C., thereby separating 68 g (0.89 mole, purity 98.2%) of glycine crystals per hour. In this secondary concentration step, water in the gaseous phase portion was purged from the system. The remaining mother liquor was analyzed, and as a result, it contained 0.97 mole per hour of hydantoic acid, glycylglycine, hydantoic amide, 2,5-diketopiperazine, hydantoin, triglycine and glycine all in terms of glycolonitrile. The mother liquor for an initial feed was prepared in this way.

Next, this mother liquor, a 50% by weight aqueous glycolonitrile solution and an aqueous solution containing the recovered carbon dioxide and ammonium were fed to a reactor so that the composition of these components might be identical with the feed composition in terms of glycolonitrile. That is, this mother liquor, 118 g (1.04 mole) of the 50% by weight aqueous glycolonitrile solution and the aqueous solution containing the recovered carbon dioxide and ammonium were fed to the reactor. The resulting reaction solution was continuously concentrated by the use of the concentrator at a concentration temperature of 130° C. for a concentration time of 10 minutes so that the concentration of glycine might be 27% by weight (the primary concentration step). A separated gaseous phase portion was cooled and condensed in order to recover 1780 g per hour of an aqueous solution of the carbon dioxide and ammonia for recycle, and this aqueous solution was then recycled to the reactor. On the other hand, 440 g per hour of the resulting concentrate (the primary condensate) was further concentrated at 130° C. for a residence time of 10 minutes so that the concentration of glycine might be 30% by weight (the secondary concentration step), so that 43 g of water in the resulting gaseous phase portion was purged. The resulting secondary concentrate was then cooled at 5° C., thereby separating 67 g of glycine per hour (purity 98.4%). A mother liquor obtained at this time was all recycled to the reactor (the composition of the mother liquor was substantially equal to that of the mother liquor for the initial feed) This amount corresponds to a glycine isolated yield of 85%. The above-mentioned operation was additionally carried out for 300 hours, and the isolation yield of glycine was heightened up to 90%. This tendency can be considered to be due to the accumulation of by-products which are in tenacious equilibrium with glycine and which can be converted into glycine.

Comparative Example 5

In Example 1, concentration was conducted in one step. That is, the resulting reaction solution was concentrated and the resulting gaseous phase portion was cooled and directly recycled to a reactor. Concentrations of ammonia and a carbon dioxide, while recovered, noticeably decreased. Therefore, it was necessary that a new aqueous ammonium carbonate solution was continuously added to the system. In this case, it was required to purge and remove as much as about 60 g of an aqueous ammonium carbonate solution per hour from the system, which amount was almost equal to that of isolated glycine, and which was unpreferable from the viewpoints of economy and environmental pollution.

EXAMPLE 5

The same procedure as in Example 1 was effected except that concentration temperature was 130° C. and concentration time was 10 minutes, in order to obtain 67 g of glycine (purity 98.3%) per hour.

EXAMPLE 6

The same procedure as in Example 1 was effected except that concentration temperature was 140° C. and concentration time was 5 minutes, in order to obtain 62 g of glycine (purity 98.5%) per hour.

EXAMPLE 7

In Example 4, glycine crystals obtained during an interval of from 80 to 150 hours were dissolved in water and then decolored with active carbon and an anion exchange resin. As a result, a glycine solution which was not colored at all was obtained. Furthermore, this solution was concentrated and crystallized, thereby obtaining glycine crystals having a purity of 99% or more which was not colored at all.

As described above, according to the process of the present invention, the accumulation of compounds in a reaction system which can be converted into glycine can be prevented by-products which are difficult to separate from glycine. In addition, an economical recycle process for effectively purging useless water can be obtained. It is fair to say that the present invention can improve the technique for manufacturing glycine via hydantoin up to an extremely advantageous level.

What is claimed is:

1. A process for preparing glycine by reacting glycolonitrile, carbon dioxide, ammonia and water in a reaction zone which comprises the steps of:

reacting glycolonitrile, carbon dioxide, ammonia and water at a high temperature in the range of 100° to 200° C. for 30 minutes to 20 hours to obtain a reaction solution containing glycine; and concentrating the thus obtained reaction solution including glycine to remove water under the conditions of a temperature in the range of 50° to 200° C. and for a time in the range of 10 seconds to 20 hours represented by the formula $$\ln(\tau) < (16800/T) - 37.8$$

wherein $\tau$ is the concentration time in minutes and T is the concentration temperature in °K. whereby substantially no diketopiperazine is formed, thereby separating substantially pure glycine and recycling at least a part of the mother liquor to the reaction zone.

2. The process for preparing glycine according to claim 1 wherein the concentration step of the reaction solution is carried out for a period of from 1 minute to 10 hours.

3. A process for preparing glycine by reacting glycolonitrile, carbon dioxide, ammonia and water without purging carbon dioxide and ammonia which comprises the steps of:

(a) feeding glycolonitrile, carbon dioxide, ammonia and water to a reaction zone and then reacting them at a temperature in the range of 100° to 200° C. for 30 minutes to 20 hours to obtain a reaction solution containing glycine;

(b) concentrating the reaction solution at a temperature in the range of 50° to 200° C. for 10 seconds to 20 hours thereby obtaining a gaseous phase portion comprising carbon dioxide, ammonia and water, and a liquid phase;

(c) recycling the gaseous phase portion to the reaction zone;

(d) further concentrating the primary concentrate at a temperature in the range of 50° to 200° C. for 10 seconds to 20 hours thereby obtaining a gaseous phase portion mainly comprising water and a liquid phase secondary concentrate;

(e) purging at least a part of the gaseous phase portion;

(f) crystallizing glycine from the secondary concentrate to obtain a slurry containing glycine crystals;

(g) separating the slurry into the glycine crystals and a mother liquor; and (h) recycling at least a part of the mother liquor to the reaction zone.

4. The process for preparing glycine according to claim 3 wherein glycolonitrile is used in the form of an aqueous solution.

5. The process for preparing glycine according to claim 3 wherein the first concentration step of the reaction solution is carried out for a period of from 1 minute to 10 hours.

6. The process for preparing glycine according to claim 3 wherein during the first concentration step of the reaction solution, 80% by weight or more of each of the carbon dioxide gas and ammonia in the reaction solution is vaporized to form a gaseous phase portion.

7. The process for preparing glycine according to claim 3 wherein the concentration of the primary concentrate is carried out at a temperature in the range of from 50° to 200° C.

8. The process for preparing glycine according to claim 3 wherein the concentration of the primary concentrate is carried out for a period of from 10 seconds to 20 hours.

9. The process for preparing glycine according to claim 3 wherein during the concentration of the primary concentrate, 10 to 90% by weight of water in the primary concentrate is vaporized to form a gaseous phase portion.

10. The process for preparing glycine according to claim 3 wherein the gaseous phase portion mainly comprising water is purged so that the amount of water corresponding to that of at least excess water may be purged.

11. The process for preparing glycine according to claim 3 wherein the secondary concentrate is cooled so as to crystallize glycine.

12. The process for preparing glycine according to claim 3 wherein at least 40% of the mother liquor is recycled to the reaction zone.

13. The process for preparing glycine according to claim 3 wherein the glycine crystals are further dissolved in water and decolored.

* * * * *